US010238785B2

(12) United States Patent
Storr et al.

(10) Patent No.: US 10,238,785 B2
(45) Date of Patent: Mar. 26, 2019

(54) MEMBRANE AND DEVICE FOR TREATING HEMOLYTIC EVENTS

(71) Applicant: Gambro Lundia AB, Lund (SE)

(72) Inventors: Markus Storr, Filderstadt (DE); Bernd Krause, Rangendingen (DE); Michael Hulko, Bondorf (DE); Oliver Amon, Tuebingen (DE)

(73) Assignee: GAMBRO LUNDIA AB, Lund (SE)

( * ) Notice: Subject to any disclaimer, the term of this patent is extended or adjusted under 35 U.S.C. 154(b) by 123 days.

(21) Appl. No.: 15/154,065

(22) Filed: May 13, 2016

(65) Prior Publication Data

US 2016/0331885 A1    Nov. 17, 2016

(30) Foreign Application Priority Data

May 15, 2015  (EP) ..................................... 15167828

(51) Int. Cl.
| | | |
|---|---|---|
| *A61M 1/34* | (2006.01) | |
| *B01D 61/24* | (2006.01) | |
| *B01D 69/08* | (2006.01) | |
| *B01D 71/68* | (2006.01) | |
| *B01D 71/40* | (2006.01) | |
| *A61M 1/16* | (2006.01) | |
| *B01D 69/02* | (2006.01) | |

(52) U.S. Cl.
CPC ........ *A61M 1/3496* (2013.01); *A61M 1/1621* (2014.02); *A61M 1/3424* (2014.02); *B01D 61/243* (2013.01); *B01D 69/02* (2013.01); *B01D 69/08* (2013.01); *B01D 71/40* (2013.01); *B01D 71/68* (2013.01); *B01D 2325/20* (2013.01); *B01D 2325/34* (2013.01)

(58) Field of Classification Search
CPC .......... B01D 69/08; B01D 61/24; B01D 1/16; B01D 1/34; B01D 2325/20; B01D 61/145; B01D 61/243; G01N 2021/3181
See application file for complete search history.

(56) References Cited

U.S. PATENT DOCUMENTS

| | | | |
|---|---|---|---|
| 4,925,299 A | 5/1990 | Meisberger et al. | |
| 2007/0251882 A1 | 11/2007 | Bradwell et al. | |
| 2012/0305487 A1 | 12/2012 | Beck et al. | |
| 2015/0314057 A1* | 11/2015 | Labib ....................... | A61M 1/34 210/323.2 |
| 2016/0331885 A1* | 11/2016 | Storr ....................... | B01D 69/08 |

FOREIGN PATENT DOCUMENTS

| | | |
|---|---|---|
| DE | 202013011936 U1 | 12/2014 |
| EP | 2161072 | 3/2010 |
| EP | 2253367 | 11/2010 |
| EP | 2862583 | 4/2015 |
| WO | WO2004/056460 | 7/2004 |
| WO | WO2012/164019 | 12/2012 |
| WO | WO2015/118045 | 8/2015 |
| WO | WO2015/118046 | 8/2015 |

OTHER PUBLICATIONS

Michael Hulke et al, "Cell-free plasma hemoglobin removal by deilayzers with various permeability profiles", SciRep; 5:16367, Published on line Nov. 10, 2015.*
Dominik J. Schaer et al, "Hemodialysis and free hemoglobin revisited: exploring hemoglobin and hemin sacavengers as a novel class of therapeutic proteins", Dec. 20, 2012; DOI10.1182/blood-2012-11-451229. Blood, Feb. 21, 2013—vol. 121, No. 8.*
Aimar, Pierre, et al., "A Contribution to the Translation of Retention Curves into Pore Size Distributions for Sieving Membranes," 1990, Journal of Membrane Science, No. 54, pp. 321-338.
Atha, Donald H., et al., "Tetramer-Dimer Dissociation in Hemoglobin and the Bohr Effect," 1976, The Journal of Biological Chemistry, vol. 251, No. 18, pp. 5537-5543.
Betrus, Christopher, et al., "Enhanced Hemolysis in Pediatric Patients Requiring Extracorporeal Membrane Oxygenation and Continuous Renal Replacement Therapy," 2007, Ann Thorac Cardiovasc. Surg., vol. 13, No. 6, pp. 378-383.
Boschetti-De-Fierro, Adriana, et al., "Extended Characterization of a New Class of Membranes for Blood Purification: The High Cut-Off Membranes," 2013, Int. J. Artif. Organs, No. 36, pp. 1-9.
Bunn, H. Franklin, et al., "The Renal Handling of Hemoglobin," 1969, United States Army Medical Research Laboratory, Blood Transfusion and Pathology Divisions, pp. 1-16.
Drabkin, David L., et al., "Spectrophotometric Studies: II. Preparations From Washed Blood Cells; Nitric Oxide Hemoglobin and Sulfhemoglobin," 1935, J. Biol. Chem., No. 112, pp. 51-65.
Granath, Kirsti A., et al., "Molecular Weight Distribution Analysis by Gel Chromatography on Sephadex," 1967, Journal of Chromatography, No. 28, pp. 69-81.
Guidotti, Guido, "Studies of the Chemistry of Hemoglobin," 1967, The Journal of Biological Chemistry, vol. 242, No. 16, pp. 3685-3693.

(Continued)

*Primary Examiner* — Ana M Fortuna
(74) *Attorney, Agent, or Firm* — Barnes & Thornburg LLP

(57) ABSTRACT

The present disclosure relates to a hemodialysis membrane for the treatment of hemolytic events, especially acute episodes of hemolysis which lead to elevated levels of plasma free hemoglobin. The present disclosure further relates to methods of removing hemoglobin from the blood of patients undergoing a hemolytic event. The treatment and method encompasses using a hemodialysis membrane which is characterized in that it comprises at least one hydrophobic polymer and at least one hydrophilic polymer and in that it has a MWRO of between 15 and 20 kD and a MWCO of between 170-320 kD, or, in the alternative, has a MWRO of between 9 and 14 kD and a MWCO of between 55 kD and 130 kD.

19 Claims, 5 Drawing Sheets

(56) References Cited

OTHER PUBLICATIONS

Lou, Song, et al., "Hemolysis in Pediatric Patients Receiving Centrifugal-Pump Extracorporeal Membrane Oxygenation: Prevalence, Risk Factors, and Outcomes," 2014, Critical Care Medicine, vol. 42, No. 5, pp. 1213-1220.
Meyer, Christian, et al., "Hemodialysis-Induced Release of Hemoglobin Limits Nitric Oxide Bioavailability and Impairs Vascular Function," 2010, Journal of the American College of Cardiology, vol. 55, No. 5, pp. 454-459.
Polaschegg, Hans-Dietrich, et al., "Red Blood Cell Damage from Extracorporeal Circulation in Hemodialysis," 2010, Seminars in Dialysis, vol. 22, No. 15, pp. 524-531.
Rother, Russell P., et al., "The Clinical Sequelae of Intravascular Hemolysis and Extracellular Plasma Hemoglobin," 2005, JAMA, vol. 193, No. 13, pp. 1653-1662.
Ward, Richard A., "Protein-Leaking Membranes for Hemodialysis: A New Class of Membranes in Search of an Application?," 2005, J Am Soc Nephrol, No. 16, pp. 2421-2430.
European Search Report and Written Opinion for EP15167828.1, completed Oct. 29, 2015.

\* cited by examiner

MEMBRANE AND DEVICE FOR TREATING HEMOLYTIC EVENTS

CROSS-REFERENCE TO RELATED APPLICATIONS

This application claims priority to European Patent Application 15167828.1, filed on May 15, 2015. The disclosure of European Patent Application 15167828.1 is hereby incorporated herein by reference in its entirety.

TECHNICAL FIELD

The present disclosure relates to a hemodialysis membrane for the treatment of hemolytic events, especially acute episodes of hemolysis which lead to elevated levels of cell-free plasma hemoglobin. The present disclosure therefore also relates to methods of removing hemoglobin from the blood of patients undergoing a hemolytic event. The treatment and method encompasses using a hemodialysis membrane which is characterized in that it comprises at least one hydrophobic polymer and at least one hydrophilic polymer and in that it has a MWRO of between 15 and 20 kD and a MWCO of between 170-320 kD, or, in the alternative, has a MWRO of between 9 and 14 kD and a MWCO of between 55 kD and 130 kD.

DESCRIPTION OF THE RELATED ART

Red blood cells normally live for 110 to 120 days. After that, they naturally break down. Hemoglobin which is released gets usually removed from the circulation by the spleen. Hemoglobin is a tetrameric protein with a molecular weight of 62 kD and is composed of 2 α and 2 β subunits. The tetramer is in equilibrium with the αβ dimer, wherein low concentrations are favorable for the dimeric state. Each subunit contains a heme group that mediates oxygen transport from the lungs to the tissues. In the body, hemoglobin is tightly confined to the intracellular compartments of erythrocytes. The intracellular hemoglobin concentration is approximately 330-360 g/L. The concentration in whole blood is normally in the range 120-160 g/L, and the cell-free plasma hemoglobin (CPH) reference range for a healthy individual is below 0.02 g/L. Plasma cell-free hemoglobin concentrations of more than 100 mg/L are perceived as critical concentrations which may require intervention. Hemoglobin is removed from plasma by binding to the hemoglobin scavenger protein haptoglobin, followed by the recognition of this complex by CD163 on the surface of monocytes, internalization by endocytosis and finally degradation. The binding capacity of haptoglobin for hemoglobin is 0.7-1.5 g/L (Rother R P, Bell L, Hillmen P, Gladwin M T. The clinical sequelae of intravascular hemolysis and extracellular plasma hemoglobin: a novel mechanism of human disease. Jama. 2005 Apr. 6; 293(13):1653-62.). Cell-free plasma hemoglobin concentrations of >0.1 g/L are generally perceived as undesirable for a patient. CPH above 0.7 g/L are beginning to overwhelm the body's abilities to address elevated CPH levels and therefore are even more critical.

Hemolytic anemia is a condition in which red blood cells are destroyed and removed from the bloodstream before their normal lifespan is over. This process is called "hemolysis". When blood cells die, the body's bone marrow usually produces new blood cells to replace them. However, in hemolytic anemia, the bone marrow can't make red blood cells fast enough to meet the body's needs, and the patient becomes "anemic" because of the high rates of red blood cell destruction. If intravascular hemolysis with binding to haptoglobin overwhelms the rate of haptoglobin synthesis, the haptoglobin levels decrease. After haptoglobin is saturated, excess hemoglobin is filtered in the kidney and reabsorbed in the proximal tubules where the iron is recovered and converted into ferritin or hemosiderin. Hemoglobinuria, a condition in which hemoglobin is found in abnormally high concentrations in the urine, indicates severe intravascular hemolysis overwhelming the absorptive capacity of the renal tubular cells. Urine hemosiderin is another indicator that intravascular free hemoglobin is being filtered by the kidneys. In addition, lactic dehydrogenase (LDH) is generally greatly elevated in patients with intravascular hemolysis. Symptoms will depend on the severity and duration of hemolysis or hemolytic anemia. Symptoms of acute hemolysis characteristically begin with an increase in temperature and pulse rate. Acute symptoms may include chills, rigors, dyspnoea, chest and/or flank pain, sense of dread, confusion, abnormal bleeding and may progress rapidly to shock, which is life-threatening. Instability of blood pressure is frequently seen. In anaesthetized patients, hypotension and evidence of disseminated intravascular coagulation (DIC) may be the first sign. This may be a fatal reaction. Midterm, patients develop oliguria, haemoglobinuria, haemoglobinaemia and arrhythmias. In some patients ongoing hemolysis may result in enlarged spleen and/or liver, an enlarged heart and even heart failure. Gallstones or an enlarged spleen may cause pain in the upper abdomen. Kidney damage may result as excess hemoglobin crystallizes and obstructs the renal tubules, producing renal shutdown and uremia. Mechanisms of toxicity include the ability of cell-free plasma hemoglobin to scavenge nitric oxide and induce vasoconstriction in various vascular beds, neutrophil activation, damage to the vascular endothelium, and the ability of cell-free hemoglobin to undergo redox cycling leading to oxidation of lipid membranes and release of F2-isoprostanes.

There are various reasons that cause hemolytic anemia. Generally, the erythrocyte membrane becomes damaged or weakened and hemoglobin is then released from the erythrocyte compartment into the plasma. Cases of hemolysis can be classified, for example, into the categories of absent, moderate and severe hemolysis, translating into CPH concentrations of <0.5 g/L, 0.5-1.0 g/L and >1.0 g/L hemoglobin, respectively. The causes of erythrocyte damage are either inherited or acquired and, in the latter case, generally comprise pathological conditions, transfusion reactions, mechanical stress and chemically or mechanically induced hemolysis.

Pathological and/or chemical conditions that can cause acute hemolysis include viral or bacterial infections and various other diseases which may lead to hemolytic events. For example, some microbes such as *E. coli* or the beta-hemolytic *streptococcus* form substances called hemolysins that have the specific action of destroying red blood cells. Other underlying causes of hemolysis include hepatitis, Epstein-Barr virus, typhoid fever, leukemia, lymphoma, tumors and liver disease. Intravenous administration of a hypotonic solution or plain distilled water will also destroy red blood cells by causing them to fill with fluid until their membranes rupture.

In a transfusion reaction or in alloimmune hemolytic anemia antibody mediated lysis of red blood cells involves triggering of the complement cascade and may cause the red blood cells to clump together and the agglutinated cells become trapped in the smaller vessels and eventually disintegrate, releasing hemoglobin into the plasma. Acute hemolytic transfusion reactions occur at an incidence of 1:76,000 transfusions and may be associated with an immunologic destruction of transfused red cells due to incompatibility of antigen on transfused cells with antibody in the recipient circulation. The most common cause is transfusion of ABO/Rh incompatible blood due to clerical errors or patient identification errors such as improper labelling of samples, administering blood to the wrong patient or testing errors. As little as 10 mL of incompatible blood can produce symptoms of an acute hemolytic reaction. ABO/Rh incompatibility occurs in about 1:40,000 transfusions. Another cause of this type of transfusion reaction can be the presence of red cell alloantibodies (non-ABO) in the patient's plasma which have not been previously identified. Occasionally a patient may have an antibody at levels below the detection capabilities of the antibody screening method or a clerical error occurs in the labelling of patient samples. Rarely is it caused by emergency uncrossmatched blood being given to an alloimmunised patient.

Snake venoms and vegetable poisons such as mushrooms or fava beans are also known acute causes of hemolysis. A great variety of chemical agents can lead to destruction of erythrocytes if there is exposure to a sufficiently high concentration of the substance. These chemical hemolytics include, for example, arsenic, lead, benzene, acetanilid, nitrites, and potassium chlorate. Agents that may cause hemolysis comprise, for example, antimalarials, e.g. primaquine, pamaquine or chloroquine; sulphonamides and sulphones, e.g. cotrimoxazole, sulfanilamide or dapsone; analgesics; antihelmints; vitamin K analogues; naphthalene.

Mechanically induced hemolysis occurs when shear forces act on the erythrocytes such that the membrane ruptures. For example, cell-free hemoglobin can be measured in the plasma of patients who have undergone cardiac bypass for coronary artery bypass grafting or aortic repair. Physical damage to red blood cells can also occur when red blood cells are damaged during heart-lung surgery or if they are exposed to extreme heat, as in a patient with severe burns. During extracorporeal blood purification high shear forces can occur when flow characteristics change rapidly at, e.g., the vascular access point, a peristaltic blood pump, sites of stagnant flow, or kinked blood lines. Extracorporeal blood flow cannot be avoided in extracorporeal blood purification therapies; consequently, CPH levels are often elevated by such treatments (Polaschegg H D. Red blood cell damage from extracorporeal circulation in HD. Seminars in dialysis. 2009 September-October; 22(5):524-31). Acute episodes of mechanical hemolysis have been reported, for example, as a side effect in pediatric patients during extracorporeal membrane oxygenation (ECMO) (Lou S, MacLaren G, Best D, Delzoppo C, Butt W. Hemolysis in pediatric patients receiving centrifugal-pump extracorporeal membrane oxygenation: prevalence, risk factors, and outcomes. Critical care medicine. 2014; 42(5):1213-20). In this study, 138 out of 207 patients exhibited signs of mild to severe hemolysis. Among the hemolytic patients, 14 had severe hemolysis with CPH levels in the range 1.18-2.05 g/L. At such concentrations, the capacity of the haptoglobin scavenging system is clearly exceeded, and adverse outcomes associated with elevated levels of CPH occurred.

In chronic hemodialysis (HD), acute episodes of hemolysis are rarely reported for single cases of the inappropriate application of therapy equipment (Polaschegg et al., 2009). However, CPH can be chronically elevated at sublethal concentrations. CPH concentrations of 196±43 mg/L have been reported in HD patients who were treated with a low-flux dialyzer (Meyer C, Heiss C, Drexhage C, et al. HD-induced release of hemoglobin limits nitric oxide bioavailability and impairs vascular function. Journal of the American College of Cardiology. 2010 Feb. 2; 55(5):454-9.). CPH was higher in such patients than in healthy controls, whereas total hemoglobin was unaffected by HD treatment. During HD treatment, CPH concentrations increased from 196±43 mg/L to 285±109 mg/L, and this increase was related to acutely blunted endothelial function, which was measured using flow-mediated dilation after a single HD session.

The treatment in case of severe hemolysis depends on the cause of such events. Of course, if a drug or infection is causing the anemia, it is important to stop the drug or recover from the infection, including appropriate medication such as antibiotics and other supportive measures. In case of autoimmune response, medication may comprise corticosteroid medication, immune globulin infusions or, in some cases, blood transfusions. In severe, acute situations where a patient is facing life-threatening conditions such as shock or disseminated intravascular coagulation and/or is threatened with long-term consequences such as nephropathy, additional measures are required which act quickly and immediately on high hemoglobin levels.

In cases of hemolysis during extracorporeal membrane oxygenation (ECMO) and related hemoglobinuria nephropathy and acute renal failure attempts have been made to combine ECMO with continuous renal replacement therapy (CRRT) which is simultaneously performed by attaching a hemofilter (Renaflo II Hemofilter, Minntech Inc.) to the ECMO circuit so that a portion of the blood in the circuit can be shunted into the hemodialyzer for the removal of excess hemoglobin (Betrus C, Remenapp R, Charpie, J, Kudelks T, Brophy P, Smoyer W E, Lin J-J, Enhanced hemolysis in pediatric patients requiring extracorporeal membrane oxygenation and continuous renal replacement therapy. Ann Thorac Cariovasc Surg. 2007; 13(6): 378-383.). However, it was shown in Betrus et al. that hemolysis may be enhanced when a hemofilter is added to an ECMO circuit at least in children with congenital heart disease following cardiac surgery.

As a consequence, new approaches to quickly act on acute, life-threatening conditions connected to hemolysis such as in cases of poisoning, infections, transfusion reactions or ECMO would be highly desirable. Appropriate hemodialysis for removing hemoglobin from blood would be a quick and immediate possibility to address such acute incidents, provided that the use of a hemodialysis filter indeed reduces hemoglobin levels instead of increasing hemolysis as reported before (Betrus et al.). In addition, chronically or recurrently elevated cell-free plasma hemoglobin concentrations such as in hemodialysis should be addressed, preferably by hemodialysis devices which show reduced hemolysis and/or which are able to significantly remove cell-free plasma hemoglobin from the blood of the patient undergoing hemodialysis treatment.

The findings of Polaschegg et al., Lou et al., Mayer et al. and Betrus et al. seem to indicate that currently available dialyzers and membranes for use in hemodialysis cannot contribute to reducing hemoglobin concentrations during either acute hemolytic episodes or chronic settings such as in hemodialysis. Based on the relevance of continually and/or immediately reducing cell-free plasma hemoglobin concentrations in the blood of a patient as evidenced by Rother et al., Meyer et al., Betrus et al. or Zager R A, Gamelin L M. Pathogenetic mechanisms in experimental hemoglobinuric acute renal failure. The American journal of physiology. 1989 March; 256(3 Pt 2):F446-55, the present inventors have focused their attention on providing hemodialysis membranes and hemodialyzers based thereon which can efficiently remove CPH from the blood of a patient and thereby reduce the concentration of CPH below critical levels. As a result of their studies, the inventors have found that newly developed membranes can be effectively used for eliminating from patients in need said cell-free plasma hemoglobin, both in acute settings such as described before and for chronic patients, such as hemodialysis patients.

In general, dialysis membranes are designed to accomplish the removal of uremic toxins and excess water from the blood of patients with chronic renal failure while balancing the electrolyte content in the blood with the dialysis fluid. The sieving property of a membrane, i.e., its permeability to solutes, is determined by the pore size and sets the maximum size for the solutes that can be dragged through the membrane with the fluid flow. The sieving coefficient for a given substance could be simply described as the ratio between the substance concentration in the filtrate and its concentration in the feed (i.e., the blood or plasma), and is therefore a value between 0 and 1. Assuming that the size of a solute is proportional to its molecular weight, a common way to illustrate the properties of membranes is by creating a sieving curve, which depicts the sieving coefficient as a function of the molecular weight. The molecular weight cut-off (MWCO) is defined as the molecular weight where the sieving coefficient is 0.1 (FIG. 1). The sieving curve determined for a polydisperse dextran mixture can be considered a standard characterization technique for a membrane. Conventional dialysis membranes are classified as low-flux or high-flux, depending on their permeability. A third group, called protein leaking membranes, is also available on some markets. These three membrane groups were described in a review by Ward (2005), J Am Soc Nephrol 16: 2421-2430. A fourth type which has emerged some time ago is the above-mentioned high cut-off or HCO membranes, which have particular characteristics (Boschetti-de-Fierro et al. (2013): "Extended characterization of a new class of membranes for blood purification: The high cut-off membranes", *Int J Artif Organs* 36(7), 455-463). A concise summary of the general classification and performance of said membranes as is shown in Boschetti-de-Fierro et al. and shall be valid also for describing the present invention. The latest step in membrane development is a membrane type which could be positioned in between the so-called high flux and high cut-off membranes. Said membranes are also referred to as "medium cut-off" membranes (see also Table I).

These membranes and how they can be prepared are described in detail in PCT/EP2015/052365. Hemodialyzers based on such membranes are described in detail in PCT/EP2015/052364.

The most evident difference among the types of membranes mentioned above is their position along the molecular weight axis. High-flux membranes have a sieving curve which reflects their ability to remove toxins of small molecular weight such as urea and also allowing some removal of relatively large toxins, such as β2-microglobulin and myoglobin. High cut-off membranes show a sieving curve located at higher molecular weights than that for the glomerular membrane. Although the high cut-off sieving profile resembles that of the glomerular membrane up to 20 kDa, the high cut-off membranes are open toward molecular weights higher than 20 kDa. This means that the high cut-off membranes allow some passage of proteins. WO 2004/056460 already discloses certain early high cut-off membranes. Advanced dialyzers with high cut-off membranes which are currently on the market are, for example, HCO1100®, septeX™ and Theralite®, all available from Gambro Lundia AB. Known uses of high cut-off membranes include treatment of chronic inflammation (EP 2 161 072 A1), amyloidosis and rhabdomyolysis and treatment of anemia (US 2012/0305487 A1), the most explored therapy to date being the treatment of myeloma kidney (U.S. Pat. No. 7,875,183 B2). In this case, the removal of the free light chains in patients with multiple myeloma on chemotherapy has allowed the recovery of kidney function in a significant number of patients. As is shown in Table I, such high cut-off membranes are characterized by a molecular retention onset (MWRO) of between 15.0 kDa and 20.0 kDa and a molecular weight cut-off (MWCO) of between 170 kDa and 320 kDa as determined by dextran sieving curves before the membrane has had contact with blood or a blood product. Due to the loss of up to 40 g of albumin per session with the above-mentioned dialyzers, high cut-off membranes will mainly be used for acute applications, although some physicians have contemplated benefits of using them in chronic applications, possibly in conjunction with albumin substitution.

The development of the before mentioned medium cut-off membranes and dialyzers fills the gap between high-flux and high cut-off dialyzers. Such semipermeable membranes are characterized by a molecular retention onset (MWRO) of between 9.0 kDa and 14.0 kDa and a molecular weight cut-off (MWCO) of between 55 kDa and 130 kDa as determined by dextran sieving curves before the membrane has had contact with blood or a blood product. Due to this very unique sieving profile the membranes considerably extend the performance of current high-flux membranes and dialyzers, as they allow for the removal of middle and large uremic solutes which cannot be addressed by the current high-flux membranes. They are, therefore, also referred to as "membranes with increased permeability". At the same time, such membranes are able to address such higher molecular weight compounds without having to face unacceptable albumin losses during treatment. As a consequence, these membrane types can be used in both acute and chronic settings. For the avoidance of doubt, the expression "membrane(s) with increased (or "extended") permeability" as used herein is equivalent with the expression "medium cut-off membrane".

The expression "molecular weight cut-off" or "MWCO" or "nominal molecular weight cut-off" as used herein is a value for describing the retention capabilities of a membrane and refers to the molecular mass of a solute where the membranes have a rejection of 90% (see above and FIG. 1), corresponding to a sieving coefficient of 0.1. The MWCO can alternatively be described as the molecular mass of a solute, such as, for example, dextrans or proteins where the membranes allow passage of 10% of the molecules. The shape of the curve depends, to a considerable degree, on the pore size distribution and is thus linked to the physical appearance of the membrane. As already mentioned, sieving curves give relevant information in two dimensions: the shape of the curve describes the pore size distribution, while its position on the molecular weight axis indicates the size of the pores. Molecular weight cut-off (MWCO) limits the analysis of the sieving curve to only one dimension, namely to the size of the pores where the sieving coefficient is 0.1. To enhance membrane characterization the molecular weight retention onset (MWRO) has been introduced for characterizing membranes such as high cut-off and medium cut-off membranes (Boschetti-de-Fierro et al.). The MWRO is defined as the molecular weight at which the sieving coefficient is 0.9, as schematically shown in FIG. 1. It is analogous to the MWCO and describes when the sieving coefficient starts to fall from 1 to 0, i.e. when the membrane starts to reject compounds of a certain size. Defining two points on the sieving curves allows a better characterization of the sigmoid curve, giving an indication of the pore sizes and also of the pore size distribution. The expression "molecular weight rejection onset" or "MWRO" or "nominal molecular weight rejection onset", as used herein, therefore refers to the molecular mass of a solute where the membranes have a rejection of 10%, or, in other words, allow passage of 90% of the solute, corresponding to a sieving coefficient of 0.9.

TABLE I

General classification of hemodialysis membranes based on dextran sieving

| Dialyzer type | Structural Characteristics | | |
|---|---|---|---|
| | MWRO [kDa] | MWCO [kDa] | Pore radius [nm] |
| Low-flux | 2-4 | 10-20 | 2-3 |
| High-flux | 5-10 | 25-65 | 3.5-5.5 |
| Protein leaking | 2-4 | 60-70 | 5-6 |
| High cut-off | 15-20 | 170-320 | 8-12 |
| Medium cut-off | 9.0-14.0 | 55-130 | 5.5 < pore radius < 8.0 |

The applicants have found that high cut-off membranes and medium cut-off membranes as defined above and in Table I can be used to effectively address acute and/or chronic hemolysis events in a patient. The high permeability of the high cut-off membranes and the extended permeability of the medium cut-off membranes for the first time allow for an increased clearance of hemoglobin from the blood of a patient in comparison to prior art dialyzers, wherein the removal of hemoglobin from the blood significantly outweighs any hemolytic effects of the dialyzer itself. More specifically, the inventors were able to show a reduction of cell-free plasma hemoglobin in simulated dialysis treatments both with the high cut-off membranes and the membranes with increased permeability, thereby demonstrating that dialyzers comprising high cut-off membranes and dialyzers comprising membranes with increased permeability (or dialyzers comprising a mix of said membrane types) enable CPH removal in acute and/or chronic settings.

SUMMARY OF THE INVENTION

It was the object of the present invention to provide for a method of treating hemolysis in a patient by removing hemoglobin from the patient's blood, comprising withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being countercurrent to the direction of flow of blood, and returning the blood into the patient, wherein the hemodialysis membrane is characterized in that it comprises at least one hydrophobic polymer and at least one hydrophilic polymer and in that it has a MWRO of between 9 and 20 kD and a MWCO of between 55-320 kD. The MWRO and MWCO values for a given membrane are based on dextran sieving experiments before blood contact of the membrane as described by Boschetti-de-Fierro et al., 2013, and in PCT/EP2015/052364.

DETAILED DESCRIPTION

Figure 1:
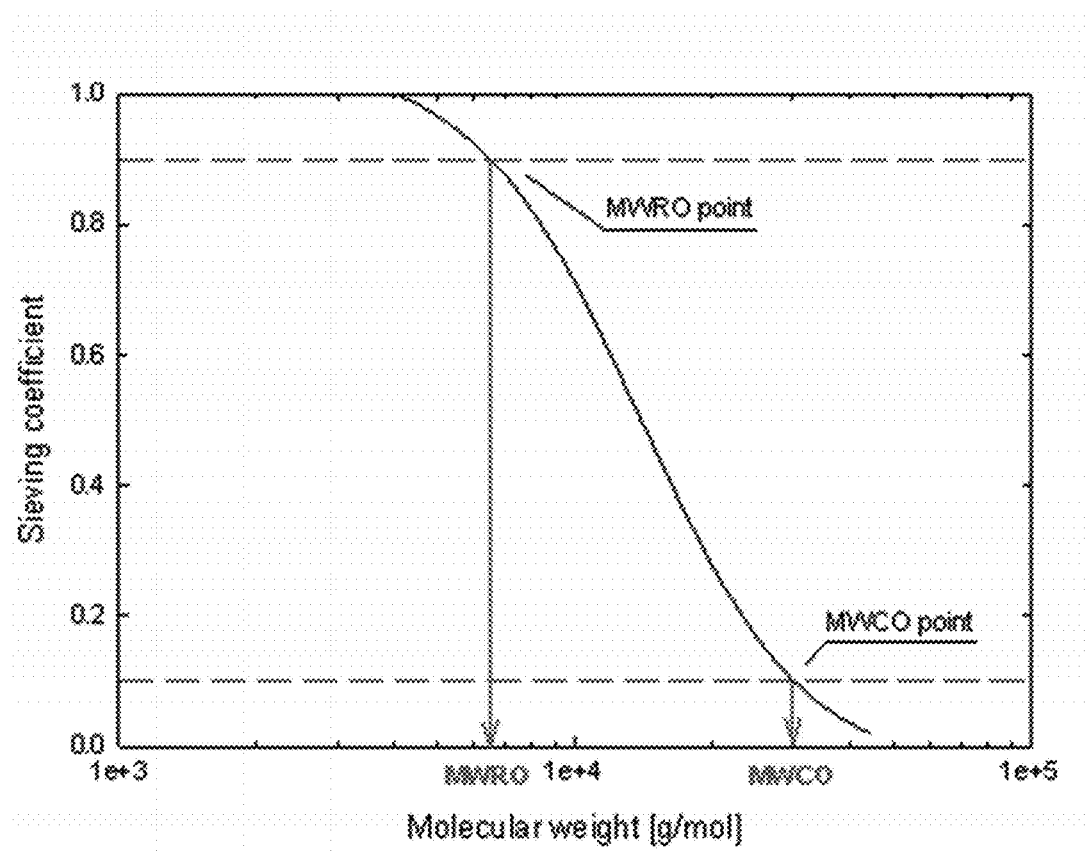
FIG. 1 is a representation of a dextran sieving curve where the values of molecular weight retention onset (MWRO, achieved at SC=0.9) and molecular weight cut-off (MWCO, achieved at SC=0.1) are illustrated.

The following numbered embodiments are contemplated and are non-limiting:

1. A semipermeable polymeric hollow-fiber membrane having a MWRO of between 9.0 and 20 kD and a MWCO of between 55-320 kD as determined by dextran sieving before blood contact of the membrane for use in a method of removing cell-free plasma hemoglobin from the blood of a patient, the method comprising withdrawing and bypassing the blood having a cell-free plasma hemoglobin concentration of above 0.1 g/L in a continuous flow into contact with one face of the membrane, simultaneously passing dialysate solution in a continuous flow on the opposite face of the membrane to the side of the membrane in contact with the blood, and returning the blood into the patient.
2. A semipermeable polymeric hollow-fiber membrane for use according to Clause 1, characterized in that the membrane comprises at least one hydrophobic polymer selected from polysulfone, polyethersulfone or polyarylethersulfone and polyvinylpyrrolidone.
3. A semipermeable polymeric hollow-fiber membrane for use according to Clause 1 or Clause 2, characterized in that the membrane has a MWRO of between 8.5 kD and 14.0 kD and a MWCO of between 55 kD and 130 kD as determined by dextran sieving before blood contact of the membrane.
4. A semipermeable polymeric hollow-fiber membrane for use according to Clause 1 or Clause 2, characterized in that the membrane has a MWRO of between 15 kD and 20 kD and a MWCO of between 170 kD and 320 kD as determined by dextran sieving before blood contact of the membrane.
5. A semipermeable polymeric hollow-fiber membrane for use according to any of Clauses 1 to 4, characterized in that the cell-free plasma hemoglobin concentration in the blood of the patient exceeds 0.7 g/L.
6. A semipermeable polymeric hollow-fiber membrane for use according to any of Clauses 1 to 5, characterized in that the sieving coefficients for hemoglobin of said membranes as determined in bovine plasma (total protein 60±5 g/L, QB=300 ml/min, UF=60 ml/min) according to DIN EN ISO 8637 are in the range of from 0.07 to 0.40.
7. A semipermeable polymeric hollow-fiber membrane for use according to any of Clauses 3, 5 and 6, characterized in that a filter device comprising same is attached to an ECMO circuit, wherein a portion of the blood in the circuit is shunted into the filter device for the removal of excess hemoglobin.
8. A semipermeable polymeric hollow-fiber membrane for use according to any of Clauses 3 and 5 to 7, characterized in that the cell-free plasma hemoglobin reduction rate in plasma based on the absorbance change at 405 nm is in the range of from 25% to 65%.
9. A semipermeable polymeric hollow-fiber membrane for use according to any of Clauses 4 to 6, characterized in that the cell-free plasma hemoglobin reduction rate in plasma based on the absorbance change at 405 nm is in the range of from 60% to 80%.
10. A semipermeable polymeric hollow-fiber membrane for use according to any of Clauses 1 to 9, characterized in that the acute hemolysis is the consequence of a viral or bacterial infection, a transfusion reaction, venoms and poisons, acute physical damage or severe burns.
11. A method of treating hemolysis in a patient by removing cell-free plasma hemoglobin from the patient's blood, comprising withdrawing and bypassing the blood from the patient in a continuous flow into contact with one face of a membrane, simultaneously passing dialysate solution in a continuous flow on an opposite face of the hemodialysis membrane to the side of the membrane in contact with the blood, and returning the blood into the patient, characterized in that the membrane is characterized in that it comprises at least one hydrophobic polymer and at least one hydrophilic polymer and in that it has a MWRO of between 9.0 and 20 kD and a MWCO of between 55-320 kD as determined by dextran sieving before blood contact of the membrane.
12. A method of treating hemolysis according to Clause 11, characterized in that the hemodialysis membrane is characterized in that it has a MWRO of between 9.0 kD and 14.0 kD and a MWCO of between 55 kD and 130 kD as determined by dextran sieving before blood contact of the membrane.
13. A method of treating hemolysis according to Clause 11, characterized in that the hemodialysis membrane is characterized in that it has a MWRO of between 15.0 kD and 20.0 kD and a MWCO of between 170 kD and 320 kD as determined by dextran sieving before blood contact of the membrane.
14. A method of treating hemolysis according to any of Clauses 11 to 13, characterized in that the cell-free plasma hemoglobin concentration in the blood of said patient is above 0.1 g/L.

In cases of hemolysis patients suffer from erythrocyte damage which is either inherited or acquired and, in the latter case, generally comprises pathological conditions, transfusion reactions, mechanical stress and chemically or mechanically induced hemolysis. Depending on the severity and duration of the hemolytic event, patients may be severely affected by the increased cell-free plasma hemoglobin concentration, including, among others, damage to the vascular endothelium, kidney damage, abnormal bleeding or shock, which is life-threatening.

The expression "hemolysis" as used herein refers to the condition in which red blood cells are destroyed before their normal life span and hemoglobin is set free from erythrocytes, leading to cell-free plasma hemoglobin concentrations of more than 0.1 g/L, especially more than 0.5 g/L.

The present disclosure therefore relates to high cut-off and/or medium cut-off hemodialysis membranes for the treatment of acute and/or chronic hemolysis in a patient by removing hemoglobin from the patient's blood. The membranes are preferably applied in cases where the cell-free plasma hemoglobin concentration (CPH) exceeds 0.1 g/L, especially where it exceeds 0.7 g/L. According to a specific embodiment of the invention, the membranes are used for treating hemolysis in a patient in need wherein the CPH exceeds 1.0 g/L. Cell-free plasma hemoglobin concentrations as used herein are determined according to the cyanmethemoglobin method for the quantitative colorimetric determination of blood hemoglobin at 540 nm based on Drabkin's reagent (D L Drabkin, J H Austin: Spectrophotometric studies: II Preparations from washed blood cells; nitric oxide hemoglobin and sulfhemoglobin. J. Biol. Chem. 1935, 112: 51-65). Drabkin's Reagent is available, for example, from Sigma-Aldrich Inc. (USA).

The method comprises withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being counter-current to the direction of flow of blood, and returning the blood to the patient, wherein the hemodialysis membrane is characterized in that it has a MWRO of between 9 and 20 kD and a MWCO of between 55-320 kD. The sieving coefficients for hemoglobin of said membranes as determined in bovine plasma (total protein 60±5 g/L, QB=300 ml/min, UF=60 ml/min) according to DIN EN ISO 8637 are in the range of from 0.07 to 0.40. According to one embodiment of the invention, sieving coefficients for hemoglobin of said membranes as determined in bovine plasma (total protein 60±5 g/L, QB=300 ml/min, UF=60 ml/min) according to DIN EN ISO 8637 are in the range of from 0.10 to 0.40. CPH clearance rates as determined in whole blood according to DIN EN ISO 8637 are in the range of from 5.0 to 30.0 ml/min. According to one embodiment of the invention, CPH clearance rates in whole blood according to DIN EN ISO 8637 are in the range of from 8.0 to 25.0 ml/min.

According to a specific embodiment of the invention, the hemodialysis membrane for treatment of hemolysis is characterized in that it is prepared from a polymer blend of polysulfone or polyethersulfone and polyvinylpyrrolidone and in that it has a MWRO of between 15 and 20 kD and a MWCO of between 170-320 kD. According to another embodiment of the present invention, the membrane for treatment of hemolysis is prepared from a polymer blend of polysulfone or polyethersulfone and polyvinylpyrrolidone and has a MWRO of between 9 kD and 14.0 kD and a MWCO of between 55 and 130 kD. The MWRO and MWCO values as used herein for a given membrane are based on dextran sieving experiments as described by Boschetti-de-Fierro et al. (2013)(see "Materials and Methods" section of the reference) and refer to values obtained before blood contact of the membrane.

According to a specific embodiment of the present invention, a membrane having a MWRO of between 9 kD and 14.0 kD and a MWCO of between 55 and 130 kD is especially useful for the continuous treatment of (anticipated) moderate to severe hemolysis, such as, for example, during extracorporeal membrane oxygenation (ECMO), continuous renal replacement therapy (CRRT), during use of ventricular assist devices or during standard hemodialysis treatment which is administered to patients suffering from end-stage renal disease. Such membranes, in the context of the present invention, are referred to as "medium cut-off membranes" or, alternatively, as "membranes having extended permeability". As mentioned before, these membranes are described in detail in PCT/EP2015/052365. The said membranes, in comparison to membranes known from the prior art, are characterized by their ability to effectively remove cell-free plasma hemoglobin, which exceeds the setting free of hemoglobin as a result of damage of erythrocytes, and by their ability to reduce the loss of albumin to insignificant levels. They can therefore be used safely over a prolonged treatment time according to the invention, either in addition to one of the critical treatments mentioned above, for example, by combining them with continuous renal replacement therapy (CRRT) which is simultaneously performed with ECMO, see also Betrus et al., or alone. For example, the treatment according to the invention can be performed by attaching a hemofilter comprising a membrane according to the present invention to an ECMO circuit so that a portion of the blood in the circuit can be shunted into the hemodialyzer for the removal of excess hemoglobin. The sieving coefficients for hemoglobin of the membranes with extended permeability as determined in bovine plasma (total protein 60±5 g/L, QB=300 ml/min, UF=60 ml/min) according to DIN EN ISO 8637 are generally in the range of from 0.07 to 0.25. According to one embodiment of the invention, sieving coefficients for hemoglobin of the membranes with extended permeability as determined in bovine plasma (total protein 60±5 g/L, $Q_B$=300 ml/min, UF=60 ml/min) according to DIN EN ISO 8637 are in the range of from 0.10 to 0.25. CPH clearance rates of membranes having extended permeability (MWRO of between 9 kD and 14.0 kD and a MWCO of between 55 and 130 kD) as determined in plasma ($Q_B$=400 ml/min, $Q_D$=500 ml/min, membrane area between 1.7 and 2.1 m$^2$) according to DIN EN ISO 8637 are in the range of from 5.0 to 15.0 ml/min. According to one embodiment of the invention, CPH clearance rates of membranes having extended permeability in plasma ($Q_B$=400 ml/min, $Q_D$=500 ml/min, membrane areas between 1.7 and 2.1 m$^2$) according to DIN EN ISO 8637 are in the range of from 8.0 to 15.0 ml/min. The CPH reduction rate in plasma based on the absorbance change at 405 nm is at least 20%, but generally is above 25%. According to one embodiment of the present invention, the CPH reduction rate in plasma based on the absorbance change at 405 nm is in the range of from 25% to 65%.

According to a specific embodiment of the invention, the above described membranes with extended permeability and hemofilters based thereon can also be used as stand-alone filters for hemodialysis treatments. In addition to performing a normal hemodialysis treatment on patients suffering from renal disease, the said membranes and filters in addition address conditions of hemolysis by effectively removing cell-free plasma hemoglobin from the blood of the patient. Accordingly, the membrane for treating hemolysis in a patient having a blood CPH concentration exceeding 0.1 g/L is prepared from a polymer blend of polysulfone, polyethersulfone or polyarylethersulfone and polyvinylpyrrolidone and has a MWRO of between 9 kD and 14.0 kD and a MWCO of between 55 and 130 kD. According to a specific embodiment of the invention, the membrane is used for treating hemolysis which is caused my mechanical stress during extracorporeal blood treatment, such as hemodialysis, ECMO or CRRT. According to another embodiment of the invention, the membrane with extended permeability has a MWRO in the range of from 9.0 kDa to 12.5 kDa and a MWCO in the range of from 55 kDa to 110 kDa. According to another aspect of the present invention, said membrane has a MWRO in the range of from 9.0 kDa to 12.5 kDa and a MWCO in the range of from 68 kDa to 110 kDa. According to yet another aspect of the present invention, said membrane has a MWRO in the range of from 10 kDa to 12.5 kDa and a MWCO in the range of from 68 kDa to 90 kDa. According to yet another aspect of the present invention, said membrane has a MWRO of more than 10.0 kDa and less than 12.5 kDa and a MWCO, of more than 65.0 kDa and less than 90.0 kDa.

A hemodialysis membrane which is characterized in that it has a MWRO of between 9 and 20 kD and a MWCO of between 55-320 kD can be effectively used especially for the treatment of acute and/or temporary hemolysis events which are characterized by a blood CPH concentration of above 0.1 g/L, specifically also for blood CPH concentrations of above 0.7 g/L, and especially for blood CPH concentrations of above 1.0 g/L. Such acute and/or temporary hemolytic events comprise the before mentioned pathological conditions, such as, for example, viral or bacterial infections (see, for example, HUS); transfusion reactions; venoms and poisons, including chemical hemolytics; acute physical damage during heart-lung surgery or severe burns. For the avoidance of doubt, the expression "acute hemolysis" refers to the immediate and rapid destruction of large numbers of red blood cells due to the aforementioned reasons, wherein the destruction occurs much faster than the body can produce new red blood cells to replace those that are destroyed, and wherein hemoglobin is released into the bloodstream, resulting in severely elevated blood CPH concentrations of above 0.5 g/L, generally even above 1 g/L. The hemoglobin concentration in such acute hemolysis events increases to said critical values in the course of below one to 24 hours and requires, among other interventions which are specific for the root cause of the hemolysis event, immediate counteractions to reduce the blood CPH concentration below values of 0.5 g/L, preferably 0.1 g/L.

According to a specific embodiment of the invention, the hemodialysis membrane for such acute hemolytic events is characterized in that it is prepared from a polymer blend of polysulfone, polyarylethersulfone or polyethersulfone and polyvinylpyrrolidone and in that it has a MWRO of between 15 and 20 kD and a MWCO of between 170-320 kD. Such membranes, which in the context of the present invention are referred to as "high cut-off" or "HCO" membranes allow for the limited passage, in whole blood, of molecules with a molecular weight of above 60 kD, including also, to a certain limited extend, albumin with a molecular weight of 68 kD. For this reason, filters based on and comprising high cut-off membranes can be efficiently used to remove hemoglobin, the 62 kD tetramer of which is in equilibrium with the αβ dimer, and which cannot be efficiently addressed with conventional dialysis based on low flux or high flux dialyzers. Due to their relatively high clearance rate for hemoglobin, which is even higher than the clearance rates for medium cut-off membranes, they can be used effectively also in cases of severe hemolysis with blood CPH concentrations of above 1.0 g/L which require a quick reduction of CPH and wherein a certain albumin loss due to the time-limited use is acceptable for the patient. CPH clearance rates of high cut-off membranes as determined in whole blood ($Q_B$=200 ml/min, $Q_D$=42 ml/min, membrane area between 1.7 and 2.1 m$^2$) according to DIN EN ISO 8637 are in the range of from 5.0 to 30.0 ml/min. According to one embodiment of the invention, CPH clearance rates of high cut-off membranes in whole blood ($Q_B$=200 ml/min, $Q_D$=42 ml/min, membrane areas between 1.7 and 2.1 m$^2$) according to DIN EN ISO 8637 are in the range of from 10.0 to 25.0 ml/min. The CPH reduction rate in whole blood based on the absorbance change at 405 nm is at least 50%. According to one embodiment of the present invention, the CPH reduction rate in whole blood based on the absorbance change at 405 nm is in the range of from 60% to 80%.

It was thus found in the present invention that in simulated treatment experiments the use of high cut-off or medium cut-off membranes leads to a significant reduction of cell-free plasma hemoglobin. Said use can be transferred to an effective treatment of patients suffering from acute hemolysis and/or to the preventive treatment of patients having a certain risk of undergoing hemolysis due to mechanical damage of their erythrocytes during extracorporeal membrane oxygenation (ECMO), continuous renal replacement therapy (CRRT), use of ventricular assist devices or standard hemodialysis treatment, respectively.

The expression "high cut-off membrane(s)" or "HCO membrane(s)" as used herein refers to membranes comprising at least one hydrophobic polymer selected from polysulfone, polyethersulfone and polyarylethersulfone and at least one hydrophilic polymer, preferably polyvinylpyrrolidone, and having a MWRO of between 15 and 20 kD and a MWCO of between 170-320 kD as mentioned before. The membranes can also be characterized by a pore radius, on the selective layer surface of the membrane, of between 8-12 nm.

The expression "medium cut-off membrane" as used herein refers to membranes comprising at least one hydrophobic polymer selected from polysulfone, polyethersulfone and polyarylethersulfone and at least one hydrophilic polymer, preferably polyvinylpyrrolidone, and having a MWRO of between 9.0 and 14.0 kD and a MWCO of between 55 kD and 130 kD, as otherwise mentioned before. The membranes can also be characterized by a pore radius, on the selective layer surface of the membrane, of more than 5.5 nm and less than 8.0 nm.

The high cut-off or medium cut-off membranes can be processed into hemodialysis filters by methods generally known in the art, for example, into hemodialysis filters having a design in terms of housing, area, fiber and bundle geometry, packing density and flow characteristics, similar to or the same as products already available on the market such as, for example, HCO1100, septeX or Theralite, both comprising HCO membranes, or as described for medium cut-off membranes in PCT/EP2015/052364. Accordingly, the use of the expression "high cut-off membrane" or "medium cut-off membrane" in the context of the present invention encompasses the use of the membrane within an adequate filter device fit for being used in/on an extracorporeal dialysis machine.

In a further embodiment of the invention, the high cut-off dialysis membrane for the treatment of hemolysis is characterized by a clearance (ml/min) for κ-FLC of from 35 to 40, and for κ-FLC of from 30 to 40 as determined in vitro (QB=250 ml/min, QD=500 ml/min; UF=0, bovine plasma, total protein 60 g/l, 37° C., membrane areas between 1.7 and 2.1 m$^2$). In yet another embodiment of the invention, the high cut-off dialysis membrane for the treatment of hemolysis are characterized by allowing the passage of molecules having a molecular weight of up to 45 kDa with a sieving coefficient of from 0.1 to 1.0 in presence of whole blood, based on EN1238 with $Q_B$ max and OF 20%. In yet another embodiment of the invention, the high cut-off dialysis membrane is characterized by sieving coefficients of from 0.9 to 1.0 for β$_2$-microglobulin and of from 0.8 to 1.0 for myoglobin, when measured according to EN 1283 with $Q_B$ max and UF 20%.

It is a further object of the present invention to provide for a method for reducing cell-free plasma hemoglobin in the blood of a patient having blood CPH concentration of above 0.1 g/L, specifically of above 0.5 g/L, comprising withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being counter-current to the direction of flow of blood, and returning the blood to the patient, wherein the hemodialysis membrane is characterized in that it comprises at least one hydrophobic polymer selected from polysulfone, polyethersulfone and polyarylethersulfone and at least one hydrophilic polymer, preferably polyvinylpyrrolidone, and has a MWRO of between 9 and 20 kD and a MWCO of between 55-320 kD. In one embodiment of the invention, said membrane is characterized in that it has a MWRO of between 9.0 and 14 kD and a MWCO of between 55 kD and 130 kD. In another embodiment of the invention, said membrane is characterized in that it has a MWRO of between 15 and 20 kD and a MWCO of between 170-320 kD. It is a further aspect of the present invention to provide for a method for reducing cell-free plasma hemoglobin in the blood of a patient having blood CPH concentration of above 0.7 g/L. It is another aspect of the present invention to provide for a method for reducing cell-free plasma hemoglobin concentration in the blood of a patient when hemolysis is diagnosed. If hemolysis is suspected, peripheral smear is examined and serum bilirubin, LDH, and ALT are measured. If results of these tests are inconclusive, urinary hemosiderin and serum haptoglobin are measured.

According to one aspect of the invention, the hemodialysis treatment regime for the reduction of elevated CPH concentration during hemodialysis of end-stage renal disease patients to values of below 0.5 g/L, preferably below 0.1 g/L, is performed with a medium cut-off membrane which has a urea clearance of at least 170 ml/min at a $Q_B$ of 200 ml/min and a $Q_D$ of 500 ml/min (UF=0 ml/min). According to yet another embodiment of the invention, the dialysis treatment especially for the regular removal of CPH during standard hemodialysis treatment according to the invention must ensure a Kt/V of >1.2. In yet another embodiment of the invention, a patient's total albumin loss does not exceed about 60 g per week, and preferably does not exceed 40 g per week. According to one aspect of the invention, the hemodialysis treatment with said medium cut-off membranes according to the invention is performed from 2 to 4 times per week for a period of from 2 to 6 hours, respectively, and thus is not different from a standard hemodialysis treatment.

According to another aspect of the present invention, a patient suffering from acute hemolysis, especially a patient having a blood CPH concentration of above 0.5 g/L, specifically above 0.7 g/L and especially those patients having a blood CPH concentration of above 1.0 g/L, is being treated, for a certain period of time, with a hemodialysis filter according to the invention which may be based on a medium cut-off or a high cut-off membrane. In one embodiment of the invention, the membrane is a high cut-off membrane, such as, for example, as it is used in existing products (septeX, Theralite). According to another aspect of the present invention the treatment may continue until cell-free plasma hemoglobin concentration has decreased to acceptable values below 0.5 g/L or preferably below 0.1 g/L. Methods for determining the blood CPH concentration in extracorporeal applications, for example, in the dialysate, are known in the art; see, for example, U.S. Pat. No. 4,925,299 A and DE 20 2013 011 936 U1.

Depending on the specific condition of a patient, such treatment regimens or routines as described above can be applied singularly or dynamically, i.e. they may be interchanged or subsequently be used for certain periods of time.

The treatment according to the invention is designed to reduce or remove cell-free plasma hemoglobin as discussed before. The amelioration of the condition of the patient based on the present treatment will allow reducing immediate risks, such as severe bleeding, shock or kidney injury, as well as long-term implications of elevated CPH concentration. The CPH mass reduction rates in whole blood upon using a high cut-off or medium cut-off membrane according to the invention at least lie in the range of more than 30% relative to the starting concentration at the beginning of a treatment. It is an object of the present invention to achieve CPH mass reduction rates in the blood of a patient of between 30% and 60%, preferably of between 40% and 60% with medium cut-off membranes according to the invention. It is another object of the present invention to achieve CPH mass reduction rates in the blood of a patient of between 50% and 90%, preferably between 60% and 80% with high cut-off membranes according to the invention.

According to one embodiment of the invention, the hemodialysis treatment according to the invention can be supplemented by a state of the art medication which would otherwise be prescribed to a patient suffering from a disease which is causally connected to hemolysis.

Dialysis machines which can be used for performing a treatment according to the invention are standard dialysis machines. Examples for such devices are the AK 96, AK 200 S and AK 200 ULTRA S, PrismafleX eXeed or the Artis dialysis machines of Gambro Lundia AB. However, any other dialysis machine having UF control can also be used for the treatment.

Parameters for performing a treatment according to the invention can be adjusted to standard dialysis treatment or medium cut-off parameters and the specifications of the high cut-off or medium cut-off membrane. Typical flow rates used for the present treatment may vary. It is advantageous to use flow rates with a $Q_B$ (blood flow) of 100-500, preferably 250-400 ml/min and a $Q_D$ (dialysate flow rate) of 100-1000, preferably 300-500 ml/min.

Methods for detecting hemoglobin in a liquid, specifically in the dialysate during treatment, are known in the art. For example, DE 20 2013 011 936 U1 discloses a device for the detection of hemoglobin during HD treatment.

Membrane passage of a solute, such as a protein which needs to be removed from blood, is described by means of the sieving coefficient S. The sieving coefficient S is calculated according to $S=(2C_F)/(C_{Bin}+C_{Bout})$, where $C_F$ is the concentration of the solute in the filtrate and $C_{Bin}$ is the concentration of a solute at the blood inlet side of the device under test, and $C_{Bout}$ is the concentration of a solute at the blood outlet side of the device under test. A sieving coefficient of S=1 indicates unrestricted transport while there is no transport at all at S=0. For a given membrane each solute has its specific sieving coefficient. In addition, the sieving curves may serve as a basis for determining, for example, the average or mean pore size or pore size distribution of a membrane on the selective layer, as there is a factual and mathematical correlation between the sieving characteristics of a membrane and its pore structure (Aimar P, Meireles M, Sanchez, V. A contribution to the translation of retention curves into pore size distributions for sieving membranes. Journal of Membrane Science 54 (1990), 321-338).

According to one aspect of the present invention, the dialysis membrane according to the invention comprises at least one hydrophilic polymer and at least one hydrophobic polymer. In one embodiment, at least one hydrophilic polymer and at least one hydrophobic polymer are present in the dialysis membrane as domains on the surface of the dialysis membrane. The hydrophobic polymer may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), polytetrafluorethylene (PTFE) or combinations thereof. In one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof. In another embodiment of the invention, the hydrophobic polymer is chosen from the group consisting of polyarylethersulfone (PAES), polyethersulfone (PES) and polysulfone (PSU). The hydrophilic polymer may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO). In one embodiment of the invention, the hydrophilic polymer may be chosen from the group consisting of polyvinylpyrrolidone (PVP), polyethyleneglycol (PEG) and polyvinylalcohol (PVA). In one embodiment of the invention, the hydrophilic polymer is polyvinylpyrrolidone (PVP).

In one embodiment of the invention, the high cut-off dialysis membrane is a hollow fiber having a symmetric or an asymmetric structure with a separation layer present in the innermost layer of the hollow fiber. In one embodiment of the invention, the dialysis membrane has at least a 3-layer asymmetric structure, wherein the separation layer has a thickness of less than 0.5 In general, the separation layer of membranes which can be used according to the invention contain pore channels having an average pore size of between about 5.0 and 12.0 nm as based on dextran sieving coefficients. In one embodiment, the separation layer contains pore channels having an average pore size of more than 7 nm, generally between 8 and 12 nm as based on dextran sieving coefficients (see also Table III of Boschetti-de-Fierro et al. (2013)). The average pore size (diameter) is generally above 8 nm for this type of membrane, which is generally referred to as "high cut-off" membrane. In another embodiment, the membrane of the invention contains pore channels having an average pore size (radius) of between about 5.0 and 7.0 nm as determined from the MWCO based on dextran sieving coefficients according to Boschetti-de-Fierro et al. (2013) and Granath K A, Kvist B E. Molecular weight distribution analysis by gel chromatography on sephadex. J Chromatogr A 28 (1967), 69-81. The average pore size (radius) before blood contact is generally above 5.0 nm and below 7.0 nm for this type of membrane ("medium cut-off" membrane) and specifically above 5.5 nm and below 6.7 nm.

The next layer in the hollow fiber membrane is the second layer, having the form of a sponge structure and serving as a support for said first layer. In a preferred embodiment, the second layer has a thickness of about 1 to 15 The third layer has the form of a finger structure. Like a framework, it provides mechanical stability on the one hand; on the other hand a very low resistance to the transport of molecules through the membrane, due to the high volume of voids. During the transport process, the voids are filled with water and the water gives a lower resistance against diffusion and convection than a matrix with a sponge-filled structure having a lower void volume. Accordingly, the third layer provides mechanical stability to the membrane and, in a preferred embodiment, has a thickness of 20 to 60 In one embodiment, the high cut-off dialysis membrane also includes a fourth layer, which is the outer surface of the hollow fiber membrane. According to one embodiment, the outer surface has openings of pores in the range of 0.5 to 3 This fourth layer preferably has a thickness of 1 to 10 μm.

The manufacturing of a high cut-off dialysis membrane follows a phase inversion process, wherein a polymer or a mixture of polymers is dissolved in a solvent to form a polymer solution. The solution is degassed and filtered and is thereafter kept at an elevated temperature. Subsequently, the polymer solution is extruded through a spinning nozzle (for hollow fibers) or a slit nozzle (for a flat film) into a fluid bath containing a non-solvent for the polymer. The non-solvent replaces the solvent and thus the polymer is precipitated to an inverted solid phase.

To prepare a hollow fiber membrane, the polymer solution preferably is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized. The precipitation process is an exchange of the solvent from the polymer solution with the non-solvent of the center fluid. By means of this exchange the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid is 30 to 80° C. The viscosity determines the kinetics of the pore-forming process through the exchange of solvent with non-solvent. The temperature in the given range should be chosen in way to be some degrees higher than the temperature which would have been chosen for the same recipe in order to obtain a standard high-flux membrane. Subsequently, the membrane is preferably washed and dried.

By the selection of precipitation conditions, e. g. temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the absorption of albumin, are avoided. The polymer solution used for preparing the membrane preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer. In one embodiment, the polymer solution coming out through the outer slit openings is, on the outside of the precipitating fiber, exposed to a humid steam/air mixture. Preferably, the humid steam/air mixture has a temperature of at least 15° C., more preferably at least 30° C., and not more than 75° C., more preferably not more than 60° C. Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5.0 wt-%, related to the water content. The effect of the solvent in the temperature-controlled steam atmosphere is to control the speed of precipitation of the fibers. When less solvent is employed, the outer surface will obtain a denser surface, and when more solvent is used, the outer surface will have a more open structure. By controlling the amount of solvent within the temperature-controlled steam atmosphere surrounding the precipitating membrane, the amount and size of the pores on the outer surface of the membrane are controlled, i.e. the size of the openings of the pores is in the range of from 0.5 to 3 μm and the number of said pores is in the range of from 10,000 to 150,000 pores/mm$^2$. A fourth layer of a high cut-off dialysis membrane is preferably prepared by this method. Before the extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols. The solvent may be chosen from the group comprising N-methylpyrrolidone (NMP), dimethyl acetamide (DMAC), dimethyl sulfoxide (DMSO) dimethyl formamide (DMF), butyrolactone and mixtures of said solvents.

Membranes with extended permeability are disclosed and can be prepared as described in PCT/EP2015/052364. Comparable membranes which can also effectively be used according to the invention and methods for preparing them are described in EP 2 253 367 A1. Dialysis filters which can be used according to the invention are shown, for example, in Table II of Boschetti-de-Fierro et al (2013) and identified as "High cut-off" dialyzer.

In conclusion, the findings of the inventors in this case demonstrate the possibility of clearing CPH from blood using extracorporeal blood purification techniques based on filters according to the invention. For example, the combination of a septeX filter with the Prismaflex system for the treatment of hemolytic events demonstrated the highest hemoglobin removal capacity in this study and might represent a suitable choice for efficient hemoglobin removal in an acute setting and for the treatment of severe hemolytic episodes. High-flux filters with extended permeability, such as the MCO-type filters used in this study and as described before in PCT/EP2015/052364 can provide for a net hemoglobin reduction in chronic dialysis settings and counteract the CPH generation that is observed as a general side effect of extracorporeal therapies. The possibility of removing CPH provides opportunities for improving patient health, as the pathophysiological effects of CPH are well described.

It will be readily apparent to one skilled in the art that various substitutions and modifications may be made to the invention disclosed herein without departing from the scope and spirit of the invention. The present invention will be illustrated by way of non-limiting examples in the Examples section in order to further facilitate the understanding of the invention.

EXAMPLES

Example 1

Materials and Methods Used for Simulated Dialysis Treatments with Blood or Plasma 1.1 Dialyzers The dialyzers used in the simulated treatments were the following: septeX 1.1 m² (Gambro Dialysatoren GmbH, Hechingen, Germany), Polyflux 170H, 1.7 m² (P170H) (Gambro Dialysatoren GmbH, Hechingen, Germany), four high-flux dialyzers with extended permeability which were prepared in accordance with PCT/EP2015/052364 (1.8 m², herein referred to as MCO1-4; Gambro Dialysatoren GmbH, Hechingen, Germany), and FX CorDiax80 1.8 m² (Fresenius Medical Care, Bad Homburg, Germany). Within the different types of MCO prototypes the permeability increased from MCO1 to MCO4. MCO 4 comprises a membrane which was prepared according to Example 1.1 of PCT/EP2015/052364. MCO 1 through 3 are based on membranes with the same recipe and the same spinning conditions, with the exception of the temperature chosen for spinning head (SH) and spinning shaft (SS), i.e. 56° C. (SH) and 53° C. (SS) for MCO 1, 57° C. (SH) and 54° C. (SS) for MCO 2, and 58° C. (SH) and 55° C. (SS) for MCO 3.

1.2 Simulated Treatment

Dialysis treatments were simulated on commercial monitor systems with a closed loop recirculation circuit on the blood side; the dialysis fluid was prepared by the monitor system from standard concentrates. Blood-side flow rate (QB), dialysate-side flow rate (QD), and ultrafiltration rate (UF) were controlled by the respective monitor systems. The system was primed with saline solution prior to the recirculation of either 1 L of heparin-anticoagulated bovine whole blood from a local slaughterhouse (Balingen, Germany) or of 1 L of bovine plasma (Kraeber & Co., Ellerbek, Germany). The total protein content in each test was 60±5 g/L, and in tests with blood the hematocrit was 32±3%. The test solution was maintained thermostatically at 37° C. throughout the experiment in a closed container. CPH was generated by adding 6 ml of freeze-thawed bovine whole blood to the test medium. Samples were collected at the start of the experiment and after 5, 20, 40 and 60 min. In one experiment, CPH was generated by adding human blood instead of bovine blood. Heparinized human whole blood was collected under medical supervision from healthy donors after written, informed consent that complied with approved local, ethical guidelines. septeX sets were tested on the Prismaflex monitor system (Gambro Lundia AB, Lund, Sweden) with blood or plasma and under 2 different flow conditions: QB 200 ml/min, QD 42 ml/min (2.5 L/h), UF 0 ml/min and QB 200 ml/min, QD 133 ml/min (8 L/h), UF 0 ml/min. There was a plasma control run at QB 200 ml/min, QD 42 ml/min, UF 0 ml/min at which addition of hemoglobin was omitted. P170H, CorDiax, and MCO1-4 were tested on the AK 200 Ultra S monitor system (Gambro Lundia AB, Lund, Sweden) with blood and QB 400 ml/min, QD 500 ml/min, OF 0 ml/min and with plasma and QB 400 ml/min, QD 700 ml/min, OF 0 ml/min. Tests of P170H, MCO1-4 and CorDiax with plasma had an initial recirculation phase of 60 min with closed dialysate ports prior to start of the experiment and hemoglobin was added after 55 min of initial recirculation. There was a plasma control run with MCO4 at which addition of hemoglobin was omitted.

1.3 Clearance Calculation

Clearance was calculated based on first-order kinetics for the variation in the plasma absorbance at 405 nm as a function of time according to Equation 1, where c(t) is the absorbance at time t, c0 is the initial absorbance, t is the time in min, Cl is the clearance in ml/min, and V is the total plasma volume in ml.

$$c(t) = c_0 \cdot e^{-t\frac{Cl}{V}} \quad \text{(Equation 1)}$$

For clearance calculations Equation 1 was transformed to Equation 2 with $A_{405}$ at the beginning of the experiment for c0, wherein t is the time of sampling after 5, 20, 40 and 60 min and $A_{405}$ at the sampling points was taken for c(t) accordingly. ln [c0/c(t)] was plotted against t/V and the clearance was calculated as the slope of a linear regression.

$$\ln \frac{c_0}{c(t)} = \frac{t}{V} \cdot Cl \quad \text{(Equation 2)}$$

In Equation 2, c(t) is the concentration at time t, c0 is the initial concentration, t is the time in min, Cl is the clearance in ml/min, and V is the total plasma volume in ml.

1.4 Plasma Sieving Coefficients

Plasma sieving coefficients were measured according to ISO norm 8637. For these tests, 1 L of bovine plasma (total protein 60±5 g/L) containing hemoglobin as the solute (6 ml of freeze-thawed bovine blood was added to 1 L of plasma) was recirculated at 37° C. with a QB of 300 ml/min and an UF of 60 ml/min. Samples were taken from the blood inlet, the blood outlet, and on the filtrate side. The sieving coefficients were calculated according to Equation 3, where SC is the sieving coefficient in [%], and $c_{in}$, $c_{out}$, and $c_F$ are the concentrations at the blood inlet, the blood outlet, and on the filtrate side, respectively.

$$SC = \frac{c_F}{\frac{c_{in} + c_{out}}{2}} \cdot 100 \quad \text{(Equation 3)}$$

1.5 Absorbance Measurements at 405 nm

Absorbance was measured photometrically at 405 nm using an Ultra Microplate Reader EL808 (BioTek Instruments GmbH, Bad Friedrichshall, Germany). The plasma samples were prepared by centrifuging blood samples and collecting the supernatant.

1.6 Hemoglobin Determination

Hemoglobin was determined in 2 ways: Absorbance was measured photometrically at 405 nm ($A_{405}$) using an Ultra Microplate Reader EL808 (BioTek Instruments GmbH, Bad Friedrichshall, Germany) detecting the Soret adsorption band of the heme molecule of hemoglobin. For better comparability of $A_{405}$ time course plots the values were normalized such that $A_{405}$ at the beginning of the experiment was set to 1. Mass concentrations were measured as a cyanide complex using the Hemoglobin FS Kit (Diasys Diagnostic Systems GmbH, Holzheim, Germany) and an Ultrospec 6300 (GE Healthcare, Frankfurt, Germany) spectrophotometer at 540 nm and a kit-specific conversion factor according to manufacturer's instructions. Measuring $A_{405}$ was used for clearance calculations because of the sensitivity of the method. The Hemoglobin FS Kit was used to verify the specificity of the $A_{405}$ measurements and to determine absolute hemoglobin concentrations. In each case the plasma samples were prepared by centrifuging blood samples and collecting the supernatant.

1.7 Calculation of the Dissociation Degree

The dissociation degree is based on the assumed equilibrium between the $\alpha_2\beta_2$ tetramer and 2 hemoglobin $\alpha\beta$ dimers and is represented as the percent ratio between the equilibrium molar dimer concentration divided by 2 and the total hemoglobin concentration of the tetramer. The equilibrium molar dimer concentration was calculated using the chemical equilibrium equation. Therefore, the molar equilibrium tetramer concentration was substituted by the total tetramer concentration minus the dimer equilibrium concentration divided by 2. The resulting quadratic equation was rearranged as Equation 4, where $c_{D;eq}$ is the dimer equilibrium concentration, $K_D$ the dissociation constant, and $c_{T;0}$ is the molar concentration of the hemoglobin tetramers.

$$c_{D;eq} = \frac{\frac{-K_D}{2} + \sqrt{\left(\frac{K_D}{2}\right)^2 + 4 \cdot K_D \cdot c_{T;0}}}{2} \quad \text{(Equation 4)}$$

The dissociation constants were obtained from the literature as follows: $K_D=5$ µM, as determined by Guidotti (Guidotti G. Studies on the chemistry of hemoglobin. II. The effect of salts on the dissociation of hemoglobin into subunits. The Journal of biological chemistry. 1967 Aug. 25; 242(16):3685-93) for CO hemoglobin in 0.2 M NaCl, pH 7 and 20° C. and $K_D=0.2$ µM, as determined by Atha and Riggs (Atha D H, Riggs A. Tetramer-dimer dissociation in homoglobin and the Bohr effect. The Journal of biological chemistry. 1976 Sep. 25; 251(18):5537-43) for oxyhemoglobin in 0.05 M cacodylate, 0.1 M NaCl, 1 mM EDTA, pH 7.2 and 20° C.

1.8 Statistics

The results presented in the tables are the mean values of the results of 3 independent replicates±the standard error of the mean. Replicates were always done as independent experiments with different dialyzer devices.

Example 2

Hemoglobin Clearance of septeX in Blood and Plasma

Figures 2A, 2B:
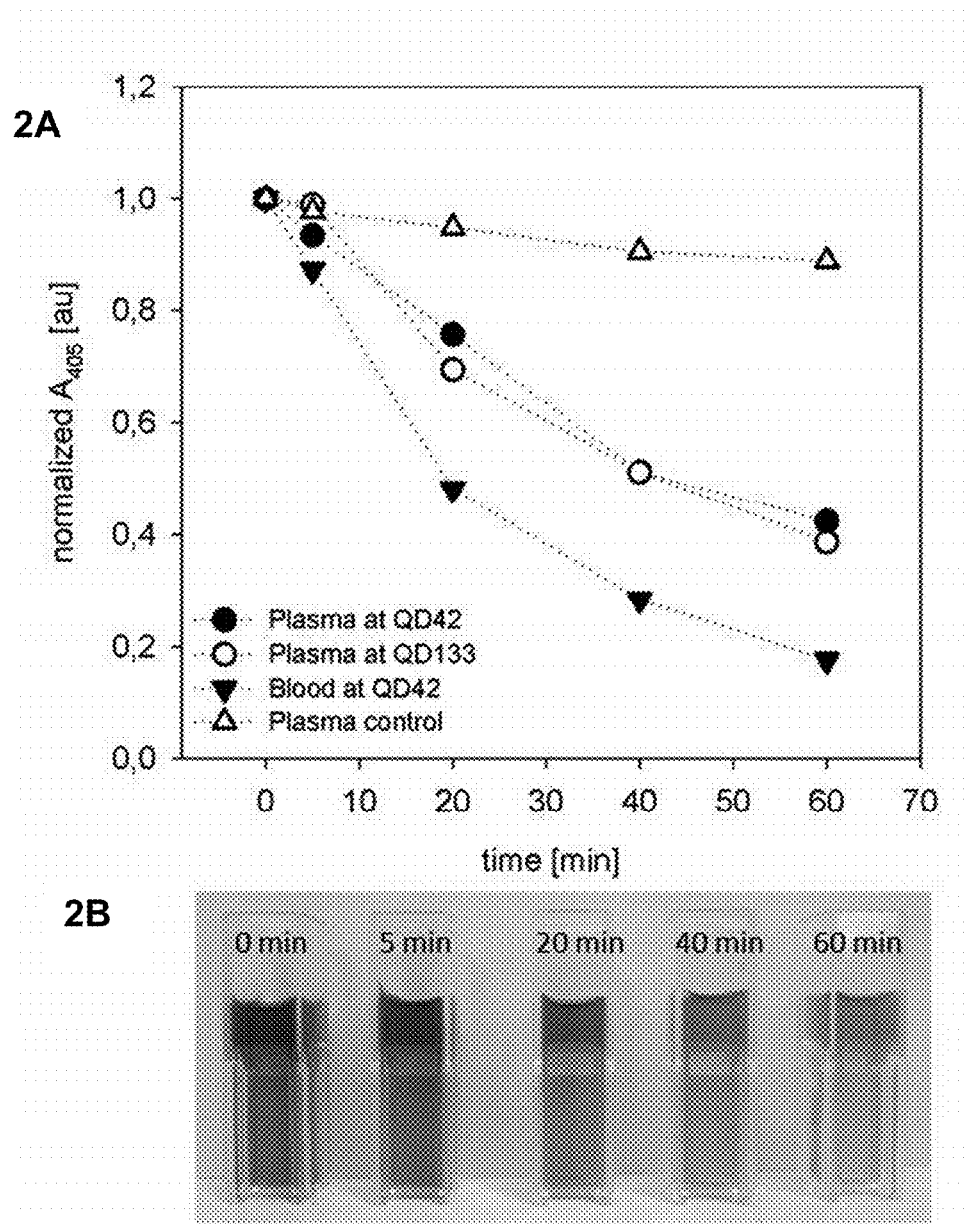
FIGS. 2A-2B show the plasma absorbance at 405 nm in arbitrary units (au) plotted versus time. The data are normalized to a value of 1 for the data point recorded at the beginning of the experiment. The plasma samples were obtained during simulated treatments with septeX™. The $Q_B$ was constant at 200 ml/min, whereas the $Q_D$ varied. The test medium was whole blood or plasma. The figure key indicates the test parameters. The plasma control represents plasma without added hemoglobin and treated using $Q_B$ 200/$Q_D$ 42 ml/min. The photograph shows plasma samples that were obtained during the whole-blood treatment.

Simulated dialysis treatments with septeX™ were conducted on a Prismaflex monitor using whole blood or plasma, and the plasma absorbance was measured at 405 nm at defined times. The plasma absorbance at the beginning of the experiment was normalized to a value of 1, and the remaining values for each experiment were related to this starting value. FIGS. 2A-2B show the time course of the plasma absorbance under various test conditions. Photographs of the plasma samples taken from the run using whole blood are shown at the bottom of FIG. 2B. When the simulated treatments were performed in the absence of CPH, the plasma absorbance at 405 nm was decreased by approximately 10% ("plasma control" in FIG. 2A). This decrease in absorbance cannot specifically be related to the decrease in CPH. Therefore, plasma control runs were taken as a baseline for the following CPH clearance calculations based on the variations of the plasma absorbance at 405 nm (Table II). The CPH mass concentration was determined at the beginning and at the end of the experiment. The removed hemoglobin mass was calculated based on the difference in hemoglobin concentration between the beginning and end of the experiment and on the plasma volume. Cell-free hemoglobin was also determined in the collected dialysate. The recovered hemoglobin mass was calculated based on the concentration of hemoglobin in the dialysate and on the collected dialysate volume. Two types of rate reductions were calculated, reflecting the changes between the beginning and the end of the simulated treatments, as follows: the reduction in the baseline-corrected absorbance at 405 nm and the reduction in the total hemoglobin mass. The results are shown in Table II.

TABLE II

Hemoglobin removal data and CPH starting concentrations in the simulated treatment experiments using septeX filters and plasma or whole blood as the test medium.

| Medium and flow rates [ml/min] | CPH clearance [ml/min] | CPH start concentration [mg/L] | Removed CPH mass [mg] | $A_{405}$ reduction rate [%] | CPH mass reduction rate [%] |
|---|---|---|---|---|---|
| Plasma QB200/ QD42 | 13.8 ± 1.8 | 668 ± 13 | 404 ± 24 | 54 ± 5.5 | 60 ± 2.5 |
| Plasma QB200/ QD133 | 15.5 ± 1.7 | 716 ± 20 | 425 ± 2.6 | 59 ± 5.6 | 59 ± 1.9 |
| Blood QB200/ QD42 | 22.6 ± 2.9 | 1045 ± 75 | 751 ± 75 | 86 ± 4.9 | 79 ± 21 |

As can be seen, the CPH clearances were between 13.8±1.8 and 15.5±1.7 ml/min in plasma and 22.6±2.9 ml/min in whole blood (Table II). The starting CPH concentrations lay in the range from 668±13 mg/L to 1045±75 mg/L. Photographs of the plasma samples show visually how the absorbance and color of the plasma changed during the simulated treatment from dark red (which is typical of hemolytic plasma) at the beginning of the experiment to light yellow (which is typical of non-hemolytic plasma) at the end of the experiment (FIGS. 2A-2B). The concentrations of CPH were higher in whole blood because the plasma volume was reduced by the volume that was occupied by the blood cells. The rate of reduction determined using the absorbance change at 405 nm and the CPH mass reduction rate are in good agreement (Table II), supporting the idea that the clearance calculation based on the absorbance changes at 405 nm was associated with the removal of hemoglobin. The recovered hemoglobin mass in the dialysate was approximately 30% lower than the calculated removed mass from the blood side. Adsorptive losses might account for the reduced recovery rate from the dialysate; however, this notion was not investigated further. The clearance in blood was higher than the clearance in plasma under identical test conditions, possibly due to the higher viscosity of blood compared to plasma, which leads to higher internal filtration and the convective transfer of CPH. In contrast to whole blood tests with high-flux dialyzers in AK 200 Ultra, the CPH generation was not observed in tests with septeX, possibly because the limited blood flow rate of 200 ml/min QB led to low levels of shear stress that did not damage erythrocytes.

Example 3

Hemoglobin Clearance of High-Flux Dialyzers in Plasma and Blood

Figure 3:
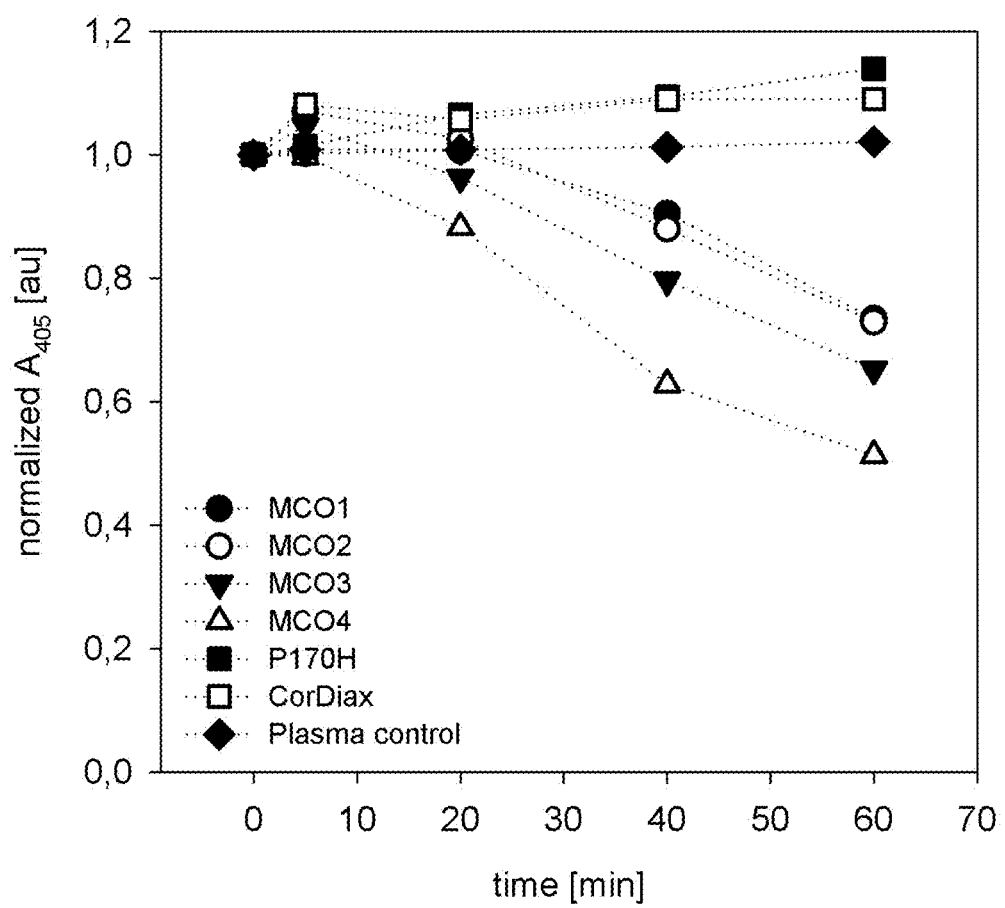
FIG. 3 shows the plasma absorbance at 405 nm in arbitrary units (au) plotted versus time. The data are normalized to a value of 1 for the data point recorded at the beginning of the experiment. The plasma samples were taken from simulated treatments using plasma with various filters as indicated in the legend. "MCO" denotes a filter comprising a membrane with increased permeability, wherein four different filter types (1-4) have been used for the experiments. The plasma control represents plasma without added hemoglobin and treated with MCO 4.

Simulated dialysis treatments with high-flux dialyzers were conducted on an AK 200 Ultra monitor using plasma and blood. The plasma absorbance at 405 nm was measured at defined times. The plasma absorbance at the beginning of the experiment was normalized to a value of 1, and the remaining values for each experiment were related to this starting value. Time courses of the plasma absorbance for the different tested filters are shown in FIG. 3 (tests using plasma) and FIG. 4 (tests using whole blood). When the simulated treatments were performed in the absence of CPH, the plasma absorbance at 405 nm remained constant ("plasma control" in FIG. 3). Therefore, absorbance changes could be related directly to decreases in CPH. In the case of CorDiax and P170H, there was a slight increase in the absorbance over time; however, for the MCO-type filters, the absorbance at 405 nm steadily decreased. CPH clearances were calculated based on variations in the plasma absorbance at 405 nm (Table III presents the results for tests using plasma, and Table IV presents the results for tests using whole blood). No clearance could be calculated for CorDiax and P170H because the absorbance slightly increased, and negative clearance values are not physically meaningful. For the test series with plasma CPH, the mass concentration was determined at the beginning and at the end of the experiment. The removed hemoglobin mass was calculated based on the difference in hemoglobin concentration between the beginning and the end of the experiment and on the plasma volume. Two types of rate reductions were calculated: the reduction in absorbance at 405 nm and the reduction of the total hemoglobin mass. The removed mass and the corresponding reduction rates were not calculated for CorDiax and P170H because no CPH removal was detected. The results of the plasma tests are shown in Table III For the test series using whole blood, the CPH mass concentration was determined at the beginning and at the end of the experiment. However, no values of mass removal were calculated because there was a certain degree of CPH generation that could not be determined separately based on the degree of hemoglobin removal. Hemoglobin starting concentrations are shown in Table IV. Cell-free hemoglobin could not be determined in the collected dialysate because the concentrations were below the quantification limit of the applied assay.

TABLE III

Hemoglobin removal data and CPH starting concentrations of the simulated treatment experiments using various filters and plasma as the test medium. The CPH clearance of MCO 4 is marked with an asterisk and was determined using human hemoglobin.

| Filter | CPH clearance [ml/min] | CPH start concentration [mg/L] | Removed CPH mass [mg] | $A_{405}$ reduction rate [%] | CPH mass reduction rate [%] |
| --- | --- | --- | --- | --- | --- |
| MCO 1 | 5.8 ± 1.2 | 577 ± 21 | 151 ± 32 | 27 ± 5.8 | 26 ± 5.1 |
| MCO 2 | 7.3 ± 1.0 | 620 ± 13 | 185 ± 36 | 27 ± 9.0 | 30 ± 6.5 |
| MCO 3 | 8.8 ± 0.6 | 616 ± 7.7 | 234 ± 42 | 35 ± 0.9 | 38 ± 6.5 |
| MCO 4 | 12.7 ± 1.7 *13.7 ± 0.8 | 438 ± 8.0 | 260 ± 1.0 | 49 ± 3.4 | 59 ± 1.2 |
| P170H | <0 | 629 ± 14 | nd | <0 | nd |
| CorDiax | <0 | 515 ± 85 | nd | <0 | nd |

TABLE IV

Hemoglobin clearance data and cell-free plasma hemoglobin starting concentrations of the simulated treatment experiments using various filters and whole blood as the test medium.

| Filter | CPH clearance [ml/min] | CPH start concentrations [mg/L] | Removed CPH mass [mg] | $A_{405}$ reduction rate [%] | CPH mass reduction rate [%] |
| --- | --- | --- | --- | --- | --- |
| MCO1 | 5.8 ± 1.2 | 908 ± 20 | 268 ± 18 | 38 ± 10 | 19 ± 2.4 |
| MCO2 | 5.4 ± 0.6 | missing data | missing data | 36 ± 5.1 | missing data |
| MCO3 | 7.5 ± 0.5 | 820 ± 6.9 | 363 ± 51 | 49 ± 4.3 | 39 ± 8.6 |
| MCO4 | 11.3 ± 1.6 | missing data | missing data | 62 ± 10 | missing data |
| P170H | <0 | 1,186 ± 42 | not determined | <0 | not determined |
| CorDiax | <0 | 970 ± 32 | not determined | <0 | not determined |

Figure 4:
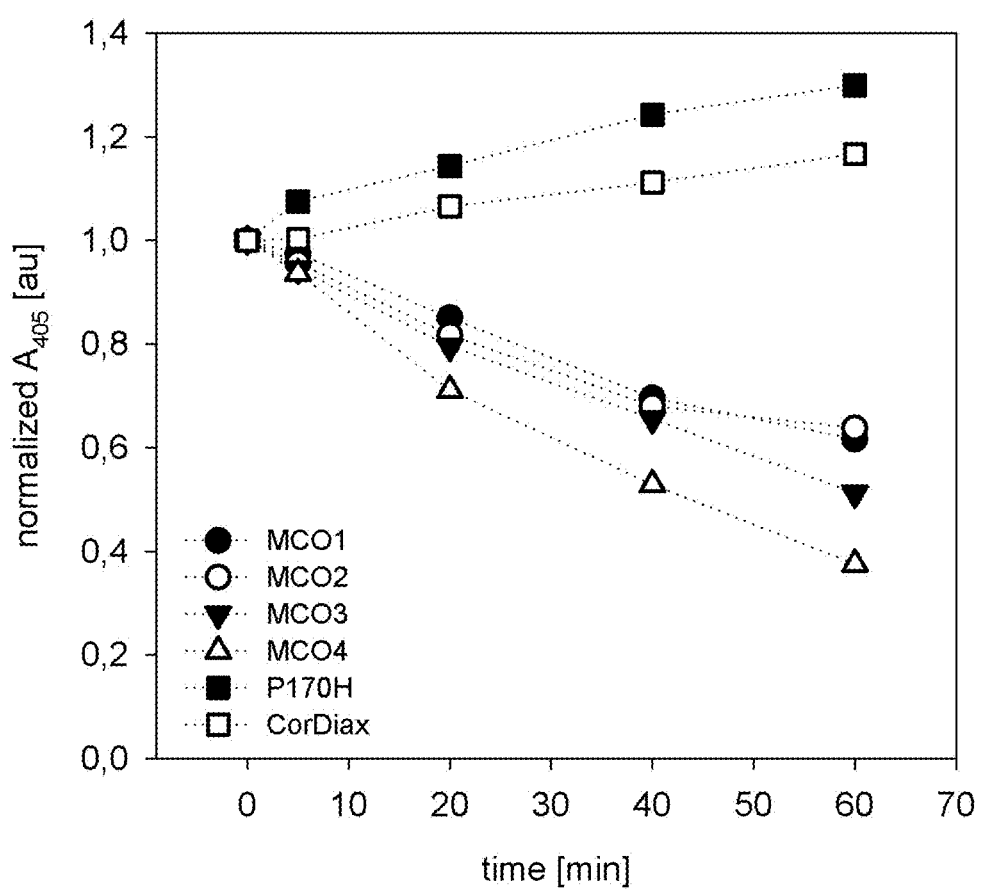
FIG. 4 depicts the plasma absorbance at 405 nm in arbitrary units (au) plotted versus time. The data are normalized to a value of 1 for the data point recorded at the beginning of the experiment. The plasma samples were collected from simulated treatments using whole blood with various filters as indicated in the key.

Simulated dialysis treatments were conducted using conventional high-flux dialyzers and high-flux dialyzers with extended permeability using an AK 200 Ultra monitor. No clearance was observed when using the conventional high-flux dialyzers P170H or CorDiax. However, high-flux dialysis filters with extended permeability (MCO 1-4) exhibited clearances of between 5.8±1.2 and 12.7±1.7 ml/min when tested using plasma and clearances of between 5.8±1.2 and 11.3±1.6 ml/min when tested using whole blood (Table III and Table IV). The starting CPH concentrations were in the range from 515±85 mg/L to 1186±42 mg/L. Again, the reduction rates that were determined using the absorbance changes at 405 nm and the mass reduction rate were in good agreement. A low degree of CPH generation might have occurred in the whole blood tests resulting from possible mechanical damage to erythrocytes in the test circuit (FIG. 3 and FIG. 4). This would explain the slight increase in absorbance for the high-flux dialyzers.

Example 4

Hemoglobin Sieving Characteristics of Membranes

Plasma sieving coefficients were determined using plasma, and the results are shown in Table V.

TABLE V

Hemoglobin sieving coefficients of the tested filters

| Filter | Sieving coefficient [%] |
|---|---|
| P170H | 1.0 ± 1.0 |
| MCO 1 | 8.8 ± 3.2 |
| MCO 2 | 12 ± 0.8 |
| MCO 3 | 16 ± 3.5 |
| MCO 4 | 21 ± 4.3 |
| septeX | 35 ± 3.4 |

The sieving coefficients were determined in plasma and were 1.0±1.0 for P170H and 35±3.4 for septeX (Table V). The sieving properties indicate that the conventional high-flux filters lack CPH permeability and therefore do not indicate CPH removal and clearance. Because CPH permeability increases with a sieving coefficient of 8.8±3.2% for MCO 1, CPH removal and clearance become measurable. For the MCO-type and septeX filters, higher sieving coefficients clearly correlated with increased CPH removal capacity.

Example 5

Dissociation Degree

Figure 5:
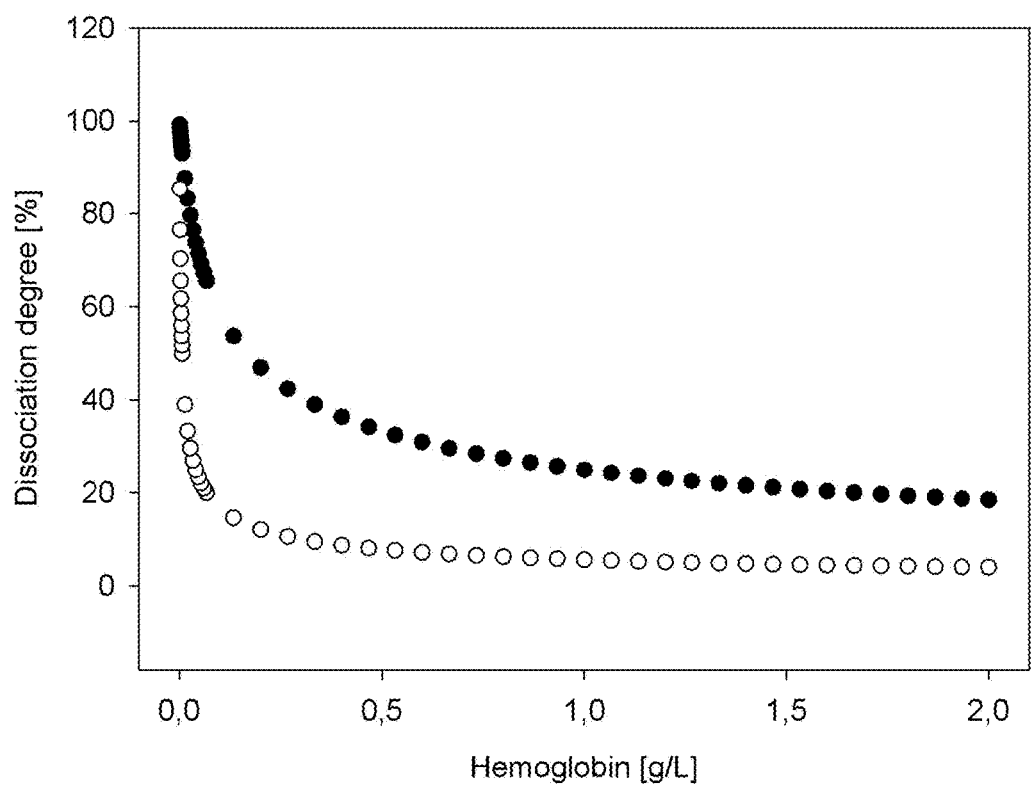
FIG. 5 depicts the dissociation degree of the hemoglobin tetramer into dimers plotted versus CPH concentration (g/L). The curves with closed and open circles were calculated using dissociation constants of KD=5 and 0.2 respectively.

The dissociation degrees for hemoglobin concentrations up to 2 g/L were calculated, and the dissociation curves are shown in FIG. 5. The degree of dissociation of the hemoglobin tetramer into dimers was calculated based on two dissociation constants reported in the literature: $K_D$=5 μM and 0.2 μM. These dissociation constants were chosen because they were considered representative of the range of dissociation constants that were reported for physiological conditions. In the concentration range that is relevant for this study (between 0.25 and 1 g/L), the dissociation degree lies between 6 and 42% (FIG. 5). While investigating glomerular filtration Bunn et al. reported a dissociation degree of approximately 25% for 1 g/L of hemoglobin which corresponds to $K_D$=5 μM) (Bunn H F, Esham W T, Bull R W. The renal handling of hemoglobin. I. Glomerular filtration. The Journal of experimental medicine. 1969 May 1; 129(5):909-23). When using the value of $K_D$=5 μM, Guidotti reported an apparent molecular weight for human hemoglobin of 55 kD, which is less than the calculated molecular weight of 62 kD of the $\alpha_2\beta_2$ tetramer, due to dissociation. The apparent molecular weight of bovine hemoglobin was calculated as 54 kD. Because the apparent molecular weights of human and bovine hemoglobin are similar, the dissociation characteristics of bovine and human hemoglobin are also likely to be similar. Thus, it is reasonable to assume that the removal capacity of bovine CPH as measured in this study is representative of and can predict the removal capacity of human CPH using the tested filters; this assumption is supported by the finding that the CPH clearance of MCO 4 is similar for bovine and human CPH (Table III). The presence of EDTA in the test solution might explain the lower dissociation constant of 0.2 μM that was reported by Atha and Riggs. The presence of bivalent ions supports the dissociation of hemoglobin. EDTA might therefore lead to a lower calculated dissociation degree. The role of bivalent ions is relevant for therapeutic applications; in particular, citrate anticoagulation might significantly change the degree of dissociation of hemoglobin and the removal capacity of the filters.

The invention claimed is:

1. A method of removing cell-free plasma hemoglobin from blood of a patient, said method comprising the steps of
   a. withdrawing and passing blood from the patient, the blood comprising a cell-free plasma hemoglobin concentration of above 0.5 g/L in a continuous flow into contact with one face of a semipermeable polymeric hollow-fiber membrane having a MWRO of between 9.0 and 20 kD and a MWCO of between 55-320 kD as determined by dextran sieving before blood contact of the membrane,
   b. simultaneously passing dialysate solution in a continuous flow on the opposite face of the membrane to the side of the membrane in contact with the blood, and
   c. returning the blood into the patient,
   wherein the method reduces cell-free plasma hemoglobin concentration to below about 0.1 g/L.

2. The method of claim 1, wherein the membrane comprises a blend of i) at least one hydrophobic polymer selected from polysulfone, polyethersulfone or polyarylethersulfone and ii) polyvinylpyrrolidone.

3. The method of claim 1, wherein the membrane has a MWRO of between 8.5 kD and 14.0 kD and a MWCO of between 55 kD and 130 kD as determined by dextran sieving before blood contact of the membrane.

4. The method of claim 3, wherein a filter device comprising the membrane is attached to an ECMO circuit, wherein a portion of the blood in the circuit is shunted into the filter device for the removal of excess hemoglobin.

5. The method of claim 4, wherein the cell-free plasma hemoglobin reduction rate in plasma based on the absorbance change at 405 nm is in the range of from 25% to 65%.

6. The method of claim 3, wherein the cell-free plasma hemoglobin reduction rate in plasma based on the absorbance change at 405 nm is in the range of from 25% to 65%.

7. The method of claim 1, wherein the membrane has a MWRO of between 15 kD and 20 kD and a MWCO of between 170 kD and 320 kD as determined by dextran sieving before blood contact of the membrane.

8. The method of claim 7, wherein the cell-free plasma hemoglobin reduction rate in plasma based on the absorbance change at 405 nm is in the range of from 60% to 80%.

9. The method of claim 1, wherein the cell-free plasma hemoglobin concentration in the blood of the patient exceeds 0.7 g/L.

10. The method of claim 9, wherein a filter device comprising the membrane is attached to an ECMO circuit, wherein a portion of the blood in the circuit is shunted into the filter device for the removal of excess hemoglobin.

11. The method of claim 1, wherein the sieving coefficients for hemoglobin of said membrane as determined in bovine plasma (total protein 60±5 g/L, QB=300 ml/min, UF=60 ml/min) according to DIN EN ISO 8637 are in the range of from 0.07 to 0.40.

12. The method of claim 11, wherein a filter device comprising the membrane is attached to an ECMO circuit, wherein a portion of the blood in the circuit is shunted into the filter device for the removal of excess hemoglobin.

13. The method of claim 1, wherein the patient has acute hemolysis.

14. The method of claim 13, wherein the acute hemolysis is the consequence of a viral or bacterial infection, a transfusion reaction, venoms and poisons, acute physical damage or severe burns.

15. A method of treating hemolysis in a patient by removing cell-free plasma hemoglobin from blood of the patient, said method comprising the steps of
   a. withdrawing and passing the blood from the patient in a continuous flow into contact with one face of a membrane, wherein the cell-free plasma hemoglobin concentration in the blood of the patient is above 0.5 g/L,
   b. simultaneously passing dialysate solution in a continuous flow on an opposite face of the hemodialysis membrane to the side of the membrane in contact with the blood, and
   c. returning the blood into the patient,
   d. wherein the membrane is characterized in that it comprises at least one hydrophobic polymer and at least one hydrophilic polymer and in that it has a MWRO of between 9.0 and 20 kD and a MWCO of between 55-320 kD as determined by dextran sieving before blood contact of the membrane,
   wherein the method reduces cell-free plasma hemoglobin concentration to below about 0.1 g/L.

16. The method of claim 15, wherein the hemodialysis membrane has a MWRO of between 9.0 kD and 14.0 kD and a MWCO of between 55 kD and 130 kD as determined by dextran sieving before blood contact of the membrane.

17. The method of claim 15, wherein the hemodialysis membrane is characterized in that it has a MWRO of between 15.0 kD and 20.0 kD and a MWCO of between 170 kD and 320 kD as determined by dextran sieving before blood contact of the membrane.

18. The method of claim 15, wherein the cell-free plasma hemoglobin concentration in the blood of said patient is above 1.0 g/L.

19. The method of claim 15, wherein the hemolysis is the consequence of a viral or bacterial infection, a transfusion reaction, venoms and poisons, acute physical damage or severe burns.

* * * * *